United States Patent [19]
Kubo et al.

[11] Patent Number: 5,236,447
[45] Date of Patent: Aug. 17, 1993

[54] ARTIFICIAL TUBULAR ORGAN

[75] Inventors: Yoshihiko Kubo, Asahikawa; Takashi Arai, Sapporo; Susumu Nakajima; Tomiyo Maeda, both of Asahikawa; Hajime Tsujikawa, Otsu, all of Japan

[73] Assignee: Nissho Corporation, Osaka, Japan

[21] Appl. No.: 723,251

[22] Filed: Jun. 28, 1991

[30] Foreign Application Priority Data

Jun. 29, 1990 [JP] Japan .................................. 2-172240
Jul. 16, 1990 [JP] Japan .................................. 2-187447

[51] Int. Cl.$^5$ ............................................. A61F 2/06
[52] U.S. Cl. ............................................. 623/1; 623/12
[58] Field of Search .................................. 623/9, 1, 12

[56] References Cited

U.S. PATENT DOCUMENTS

| | | | |
|---|---|---|---|
| 4,553,545 | 11/1985 | Maass et al. | 128/341 |
| 4,731,073 | 3/1988 | Robinson | 623/1 |
| 4,878,906 | 11/1989 | Lindemann et al. | 623/1 |
| 4,990,158 | 2/1991 | Kaplan et al. | 623/1 |

FOREIGN PATENT DOCUMENTS

| | | | |
|---|---|---|---|
| 0108171 | 10/1982 | European Pat. Off. | 623/1 |
| 0334024 | 2/1989 | European Pat. Off. | |
| 0334045 | 2/1989 | European Pat. Off. | |
| 0335341 | 3/1989 | European Pat. Off. | 623/1 |
| 0364787 | 9/1989 | European Pat. Off. | 623/1 |
| 2541888 | 9/1984 | France | 623/1 |

OTHER PUBLICATIONS

The British Journal of Surgery, Ronald Belsey, pp. 200-205 (1946).
Experimental Studies..., Rollin A. Daniel, Jr. et al, pp. 426-441, vol. XVII (Apr. 1950).
Prosthetic reconstruction of ...; The Journal of Thoracic and Cardiovascular Surgery, William E. Neville, et al, pp. 525-538.

Primary Examiner—David Isabella
Assistant Examiner—Debra S. Brittingham
Attorney, Agent, or Firm—Birch, Stewart, Kolasch & Birch

[57] ABSTRACT

An artificial tubular organ composed of a tubular supporting frame made of a plastic material which is provided on at least one surface therefore with a medical prosthetic material. The supporting frame is composed of a plurality of ring portions arranged on an axis, and a plurality of pairs of connecting portions extending between adjacent two ring portions so as to connect them to each other, every other pair of the connecting portions being diametrically arranged on the ring portions, the remaining pairs of the connecting portions being arranged such that a plane containing their center lines is perpendicular to a plane containing the center lines of pairs of diametrically arranged connecting portions. The medical prosthetic material may be a woven fabric, a knitted fabric, a nonwoven fabric, or a combination thereof. Preferred fabric includes absorbable macromolecular yarns and nonabsorbable macromolecular yarns.

22 Claims, 6 Drawing Sheets

ARTIFICIAL TUBULAR ORGAN

FIELD OF THE INVENTION

The present invention relates to an artificial tubular organ and, more particularly, to an artificial tubular organ for use in substitution or reconstruction of tubular organs such as blood vessels, tracheae and esophagi.

BACKGROUND OF THE INVENTION

Recently, the development of artificial tubular organs has been energetically pushed forward to use them as a substitute for tubular organs such as blood vessels, tracheae and esophagi, and many clinical applications of such artificial organs have been reported in the medical field.

For the artificial tubular organs used as a substitute of tubular organs with a skeleton (cartilage) such as tracheae and bronchi, Belsey, R. has reported in British J. Surg. 38 200 (1950), clinical trials employing a stainless steel wire closely wound in the form of a helix and covered with a fascia, and Daniel, R. A et al have reported in Dis. Chest. 17 426 (1950) on experiments using a glass tube. These reports initiated the development of artificial tubular organs, and various investigations have been made on artificial tubular organs of a wide variety of materials.

In general, the requirements common to artificial tracheae are to have sufficient resistance to deformation, to cause no leakage of air, and to be incorporated into organisms without causing significant inflammatory response. To meet these requirements, many studies have been conducted on materials for artificial tracheae, and their structure. The most artificial tracheae of the prior art are in the form of meshes or solid tubes, but the investigations in recent years are directed to artificial organs composed of a supporting frame covered with a mesh such as woven fabrics or knitted goods.

In J. Thoracic & Cardovasc Surg. 72 525 (1976), Neville has stated the following six conditions are required for an ideal artificial trachea:

(1) to be airtight to avoid leakage of expired air and inspired air;
(2) to have a suitable mechanical strength and resistance to deformation to avoid occlusion of the trachea by pressure;
(3) to be taken in by the organism,
(4) to be incorporated into the surrounding organisms with less inflammatory response;
(5) to prevent fibroblasts from passing therethrough as well as to prevent bacteria from making an invasion into the lumen; and
(6) to permit ingrowth of respiratory epithelia along the lumen.

However, there is no artificial trachea which satisfies all these conditions, especially, the conditions (3), (4) and (6) simultaneously.

For example, the artificial tracheae as shown in FIGS. 9 and 10, known as arched grafts, involve a problem in the condition (3). Since such artificial tracheae generally comprise a mesh reinforced by a supporting frame 31 with a semicircular cross section shown in FIG. 9 or 10, they are poor in longitudinal extension and contraction. This causes abrasion or releasing from the surrounding tissue, resulting in failure to be taken in by the organism.

In Japanese patent national publication No. 2-501118, it has been proposed to use an artificial blood vessel comprising a medical prosthetic material of a tubular woven fabric constructed by alternately performing plain weave and twill weave. This artificial blood vessel is improved in softness and flexibility and may be used without performing coating of a coagulant. However, the softness is lost from the blood vessel by the adhesion with the surrounding tissues, so that the blood vessel cannot follow with the movement of the body, thus causing inflammation of the tissue.

Japanese patent lying-open No. 57-115250 discloses an artificial tubular organ coated with a blood coagulation factor XIII (or fibrin stabilizing factor), which is used as an artificial trachea to be implanted in a resected portion of the trachea invaded by cancer or in a resected portion of bronchus affected with a tumor. This artificial tubular organ causes no risks such as obstructive thrombus, formation of ulcer or stenochoria as the rate of organization just after implantation is improved by the blood coagulation factor XIII.

However, the woven fabric or knitted goods used as the medical prosthetic materials for artificial tubular organs have the following disadvantages. If the fabric has a low compactness, the prosthetic material possesses good softness, but it permits the internal air to pass there-through and then intrudes into the tissue, causing inflammation due to microbism. If the prosthetic material is composed of a woven or knitted fabric of a compact construction, or of a fabric provided with a coating to give good airtightness and watertightness, the artificial tubular organ becomes rigid, does not fit to the surrounding tissue, prevents invasion of endotheliums, and causes disturbances in the surrounding tissue.

Commercially available artificial tubular organs comprise a silicone wire closely wound in the form of a helix and covered with a fabric to prevent the leakage of expired air or inspired air. In such an artificial trachea, however, the granulation tissue is prevented from entering into the medical prosthetic material. Thus, the artificial trachea is prevented from incorporation into the surrounding tissue so that the migration of the artificial trachea occurs.

SUMMARY OF THE INVENTION

It is therefore an object of the present invention to provide an artificial tubular internal organ having high resistance to deformation and good airtightness, and capable of being incorporated into the tissue after implantation to provide good adhesion with the surrounding tissues.

The above and other objects of the present invention are achieved by providing an artificial tubular organ composed of a tubular supporting frame made of a plastic material and provided on its at least one surface with a medical prosthetic material, said supporting frame being composed of a plurality of ring portions arranged on an axis, and plural pairs of connecting portions extending between neighboring two ring portions to connect them to each other, every other pair of said connecting portions being diametrically arranged on said ring portions, the remaining pairs of said connecting portions being arranged such that the plane containing their center lines intersects at a right angle with the plane containing the center lines of the diametrically arranged connecting portion pairs, said medical prosthetic material being composed of at least one fabric selected from the group consisting of woven fabrics, nonwoven fabrics, and knitted fabrics.

As a material for the supporting frame, there may be used any biocompatible synthetic resins. Typical biocompatible synthetic resins include, without being limited to, olefin resins such as polyethylene, polypropylene; fluoroplastics such as polytetrafluoroethylene, ethylene-tetrafluoroethylene copolymers, polychlorotrifluoroethylene; and polyesters.

In a preferred embodiment, each pair of the connecting portions of the tubular supporting frame are diametrically arranged on the ring portions.

As a medical prosthetic material, there may be used any known fabrics including woven fabrics, nonwoven fabrics and knitted fabrics. It is, however, preferred to use a partially absorbable fabric comprising absorbable macromolecular yarns and nonabsorbable macromolecular yarns. Such a fabric may be used alone or in combination with any known fabrics comprising nonabsorbable macromolecular yarns or fibers. When a fabric comprising absorbable yarns is used in combination with a fabric made of nonabsorbable yarns, it is preferred that the former is sandwiched between the supporting frame and the latter.

The above partially absorbable woven fabric may be constructed by composite yarns composed of at least one absorbable macromolecular yarn and at least one nonabsorbable macromolecular yarn. Such composite yarns may be prepared by yarn doubling or twisting. Also, the fabric may be a union or knitted fabric composed of absorbable macromolecular yarns and nonabsorbable macromolecular yarns.

The yarns for woven fabrics, nonwoven fabrics, knitted fabrics may be monofilament yarns or multifilament yarns. The most preferred yarns are false twist yarns as they improve airtightness and flexibility of the produced fabrics.

As a material for the nonabsorbable macromolecular yarns, there may be used those such as polyesters (e.g., polyethylene terephthalate); polyolefins (e.g., polyethylene polypropylene); polyamide resins (e.g., 6-nylon, 66-nylon); fluoroplastics (polytetrafluoroethylene, polyvinylidene fluoride); chlorine resins (e.g., polyvinylchloride, polyvinylidene chlorides); polyurethane resins; cellulose derivatives; or natural fibers. Among them it is preferred to use polyolefins since the granulation tissues firmly adhere to yarns of polyolefin fibers but never enter into the lumen of the supporting frame and thus provide no disturbance of the flow of blood or air.

As a material for the absorbable macromolecular yarns, there may be used those such as polylactide, polyglycolic acid, polyvinyl alcohol, polyacryl amide, polyvinyl pyrolidone, poly-γ-methyl-glutamade, polycaprolactone, polydioxanone and derivatives thereof, ethylene-carbon monoxide copolymers, cellulose derivatives or copolymers thereof, vinyl acetate-unsaturated carboxylic acid copolymers, and the like.

The above fabrics or composite yarns may be coated with a protein. Typical proteins includes, without being limited to collagen, gelatin, fibrinogen, globulin, and fibronectin. The protein coatings may be formed by immersing woven fabrics, non-woven fabrics or composite yarns in a protein solution and then rinsing them with water several times at room temperature.

The woven or nonwoven fabric comprises absorbable macromolecular yarns which are dissolved and absorbed in the organism to form openings or pores in the fabric after implantation. Preferably, the openings or pores to be formed in the fabric of at least the nonabsorbable macromolecular yarns after implantation have an average diameter of 110 μm and are present at least 20% in the fabric.

The artificial tubular organ of the present invention is capable of being bent in any directions, back and forth or to the left and right, because of a new construction of the tubular supporting frame. It is possible to make a discrimination in the bending angle of the artificial tubular organ between back and forth directions by suitably selecting the location of the odd numbered or even numbered connecting portions in a pair.

The provision of the connecting portions makes it possible to prevent the supporting frame from excess expansion in the axial direction, as well as to prevent aberration of the ring portions, thus making it possible to improve the resistance to deformation.

Further, the stitches joining the fabric with the supporting frame are limited in movement by the connecting portions, thus making it possible to avoid the deviation of the fabric from the given position on the tubular supporting frame.

Just after implantation of the artificial tubular organ, the medical prosthetic material of the woven, knitted, or nonwoven fabric prevents movement of substances such bacteria. With the lapse of time, however, the absorbable macromolecular yarns constituting the fabric are decomposed and absorbed in the organism so that numerous pores or openings are formed in the fabric. For this reason, the granulation tissues surrounding the artificial tubular organ enters into openings and grow up to form organism, while closing the openings of the fabric. As a result, the fabric with a rough texture composed of the remaining nonabsorbable macromolecular yarns forms a dense composite with the organism.

The above and other objects, features and advantages of the present invention will be further apparent from the following description taken in conjunction with the accompanying drawings.

PREFERRED EMBODIMENT OF THE PRESENT INVENTION

Figure 1:
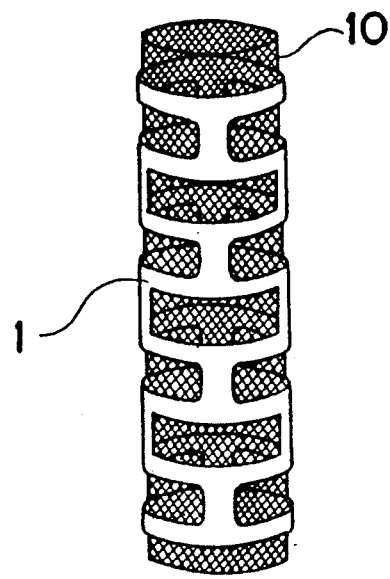
FIG. 1 is a perspective view of an artificial tubular organ embodying the present invention.

Referring now to FIG. 1, there is shown an artificial tubular organ embodying the present invention, which comprises a tubular supporting frame (1) made of a plastic, and a medial prosthetic material (10) arranged in the lumen of the supporting frame (1) and joined thereto with several stitches.

The supporting frame (1) is made of a biocompatible synthetic resin in the form of a cylinder shape of a 5 to 30 mm length. This frame (1) comprises a plurality of ring portions (2) arranged on a common axis, and plural pairs of connecting portions extending between neighboring two ring portions to connect them each other.

The ring portions (2) constitute a side wall of the supporting frame (1) so that they are required to have a suitable compressive strength to prevent crushing of the artificial tubular organ, for example, artificial trachea after implantation into the organism. Although the compressive strength of the supporting frame varies with a thickness of the ring portions and a raw material used, the artificial trachea is generally designed such that it possesses the compressibility ranging from about 5 to 25% when a load of 500 g is applied to the artificial trachea of 5 cm in length in the direction perpendicular to its axis. The ring portions may have any cross sections such as circular, square, or rectangular, but it is preferred that they have a rectangular cross section.

The connecting portions (3) are formed as an integral part of the supporting frame (1). A length of the connecting portions (3) is so determined that it is smaller than a radius of the ring portions (2). The connecting portions may have any thickness as occasion demands, but it is preferred that they have a thickness substantially the same as that of the ring portions (2), taking account of the mechanical strength and easiness of molding.

The connecting portions (3) in pairs are diametrically arranged between the neighboring two ring portion (2) so that they are either above or below next connecting portion (3) but one. Thus, the connecting portions (3) in pair are symmetric with respect to the axis of the supporting frame (1), but odd numbered pairs of said connecting portions (3) are arranged such that the plane containing their center lines intersects at right angles with the plane containing the center lines of even numbered pairs of the connecting portions.

Figure 3A:
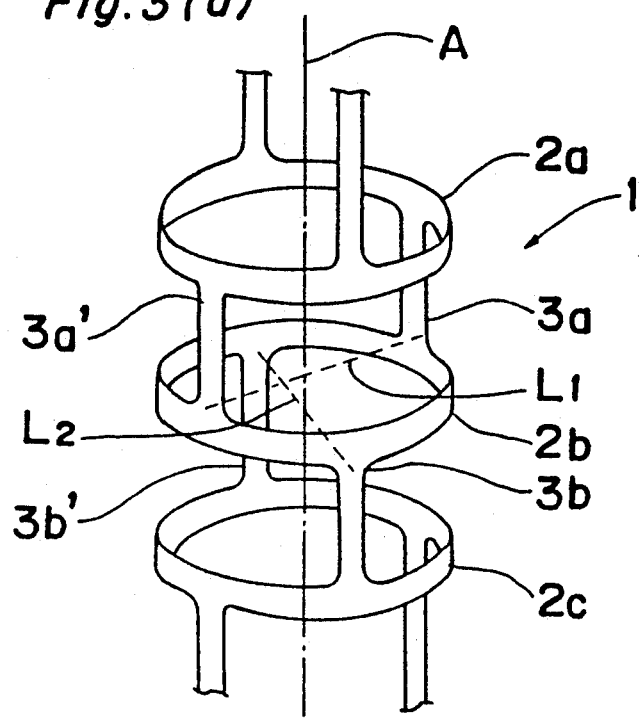
FIG. 3a is an enlarged perspective view of the supporting frame of FIG. 2.

As fully illustrated in FIG. 3, the position of a pair of the connecting portions (3) with respect to an upper or lower pair of the connection portions (3) is determined such that a straight line ($L_1$), which connects the intersections of each of the connecting portions ($3a$, $3a'$) in pairs and the ring portion ($2b$), extends in the direction perpendicular to a straight line ($L_2$) which connects the intersections of each of the connecting portions ($3b$, $3b'$) in pair and the ring portion ($2b$). Also, each straight lines ($L_1$, $L_2$) intersect at right angles with the axis (A) of the supporting frame (1).

Figure 4:
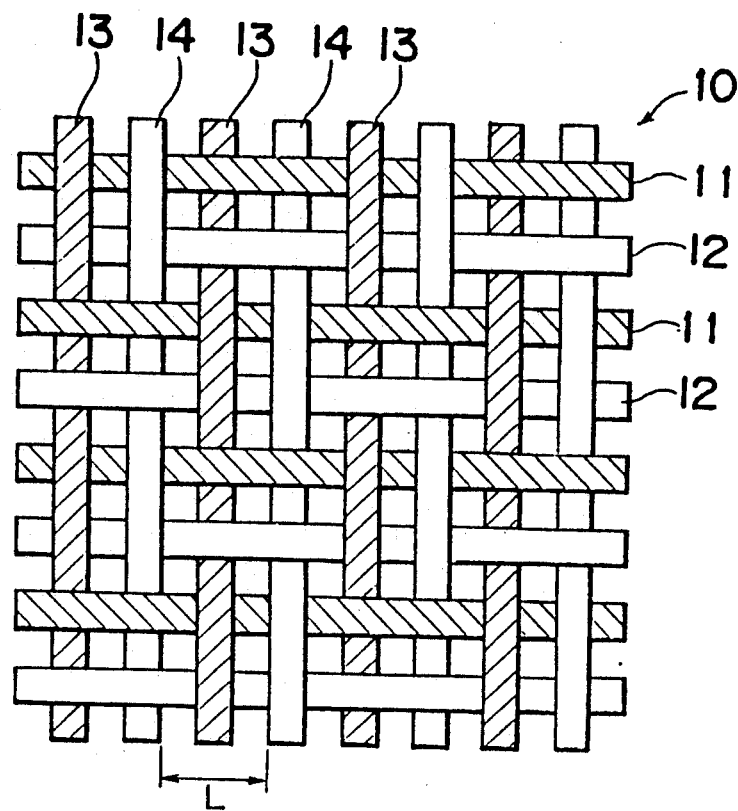
FIG. 4 is a fragmentary plan view of a medical prosthetic material composed of a woven fabric used in the artificial tubular organ of FIG. 1.

FIG. 4 shows the prosthetic material (10) composed of a woven fabric having a plain weave construction in which weft yarns (11, 12) pass alternately under and over warp yarns (13, 14) across the width of the fabric. One of the weft yarns, i.e., weft yarns (11) are absorbable macromolecular yarns, while the other weft yarns 12 are nonabsorbable macromolecular yarns. Similarly, one of the warp yarns 13 are absorbable macromolecular yarns, while the other warp yarns 14 are nonabsorbable macromolecular yarns.

In order to fix (immobilize) the implanted artificial tubular organ in the body, the artificial tubular organ is required to form pores in the textile after implantation so that granulation tissue enters into pores to form an inner structure rapidly. According to the present invention this is achieved by combined use of absorbable macromolecular yarns and nonabsorbable macromolecular yarns. The absorbable yarns are dissolved and absorbed in the body, thereby forming pores between the remaining nonabsorbable macromolecular yarns.

It is preferred that an average diameter of the produced pores is at least 110 $\mu$m, preferably, 300 to 1500 $\mu$m. Further, it is preferred that the pores of at least 110 $\mu$m present in the textile occupies least 20%, preferably, 40 to 70% of the surface area of the textile. If the average diameter of the pores is less than 110 $\mu$m, it is difficult for the granulation tissue to enter into pores between the fibers of the textile, causing failure in immobilization of the fiber structure in the body.

The above medical prosthetic material (10) or woven fabric is joined to the supporting frame (2) with several stitches. The stitching thread is composed of the same materials as materials of the fabric, i.e., absorbable macromolecular yarns and nonabsorbable macromolecular yarns.

When such an artificial tubular organ is implanted in the body, one of the constituents of the prosthetic material, i.e., absorbable macromolecular yarns are decomposed by breakage of their main chains of chemical structures and absorbed in the body to form openings or pores between non-absorbable macromolecular yarns, into which the granulation tissues enter into the openings or pores so that the artificial tubular organ firmly adheres to the surrounding tissues and is fixed thereto. Since the artificial tubular organ is required to have good airtightness and watertightness, the medical prosthetic material is constituted by a woven fabric with a high density. For this reason, the artificial tubular organ is initially stiffened, but it is then softened with the lapse of time as the absorbable macromolecular yarns are dissolved and absorbed in the body. This makes it possible to minimize an obstacle due to implantation as well as to avoid occurrence of inflammation.

In the above embodiment, all the pairs of the connecting portions (3) are diametrically arranged so that they are symmetric with respect to the axis of the supporting frame (1). However, this is not necessarily required. It is sufficient to make one of the straight lines ($L_1$, $L_2$) intersect perpendicularly to the axis (A) of the supporting frame (1).

Figure 3B:
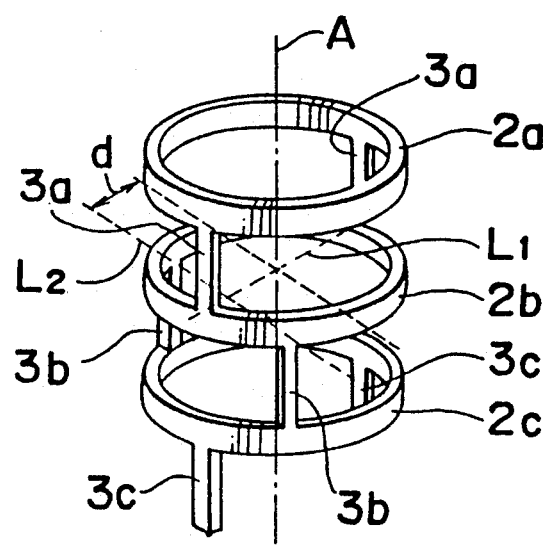
FIG. 3b is an enlarged perspective view showing a modified form of the supporting frame of FIG. 2.

FIG. 3b shows modification of a tubular supporting frame for use in the artificial tubular organ of the present invention. In this embodiment, one of the straight lines ($L_1$, $L_2$), for example, the straight line ($L_1$) is separated by a distance (d) from the straight line ($L_3$) passing the axis (A) in parallel thereto. For this reason, the bending angle of the supporting frame (1) is greatly affected by the distance d between the axis (A) and the line ($L_1$). The greater the distance d, the smaller is the bending angle in the direction of an arrow $-X$, as indicated in FIG. 3b. However, this makes it easy to bent the supporting frame (1) in the opposite direction, i.e., in the direction of an arrow X in FIG. 3b. Thus, the bending angle of the supporting frame (1) may be determined according to a sort of artificial organs to be produced or objects to be implanted.

In the above embodiment, the prosthetic material is composed of a textile of the plain weave structure, but weaves of the textile are not limited thereto. There may be used textiles or fabrics constituted by any other weaves including twill weave, sateen weave and respective variations. Also, there may be used tubular or flat knitted goods such as, for example, warp knitted fabrics, weft knitted fabrics, plain stitch fabrics, interlock fabrics, fleecy fabrics, and tuck stitch fabrics.

Figure 5:
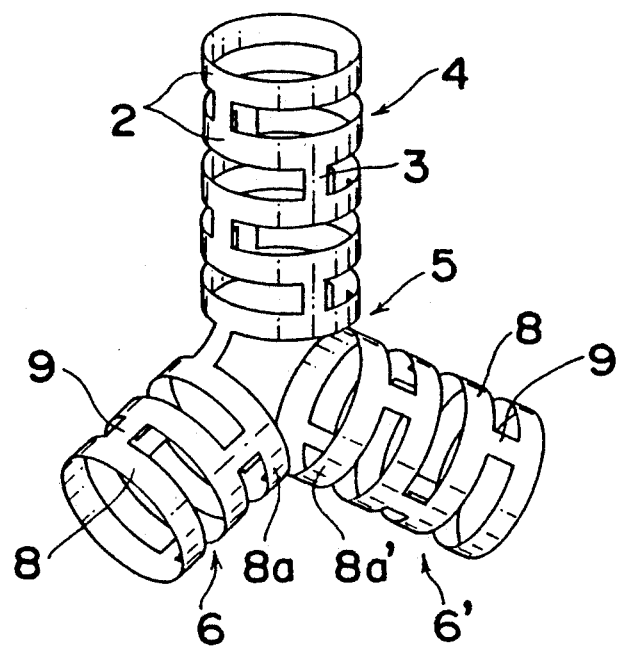
FIG. 5 is a perspective view of a supporting frame used in the artificial trachea according to the present invention.

FIG. 5 shows a modification of a tubular supporting frame for use in the artificial trachea of the present invention. This supporting frame is made of a biocompatible synthetic resin in the form of inverted Y-shape, and is composed of a trachea portion (4), a bifurcated portion (5), and bronchus portions (6, 6'). The trachea portion (4) comprises a plurality of ring portions (2) arranged on a common axis, and plural pairs of connecting portions (3) extending between neighboring two ring portions (2) to connect them each other. Similarly, each bronchus portion (6, 6') is composed of a plurality of ring portions (8) arranged on a common axis, and plural pairs of connecting portions (9) extending between neighboring two ring portions (8) to connect them each other.

The lowermost ring portion (2) is connected to the uppermost ring portions (8) of the bronchus portions (6) by a pair of a connecting portion extending therefrom to form a bifurcated portion (5), and the uppermost ring portions (8a, 8a') are connected each other at their edges. The left bronchus portion 6' (in FIG. 5, right portion) extends sideways at an angle smaller than that of the right bronchus portion (6), but has a length longer than that of the right bronchus portion (6).

The above tubular supporting frame is covered with a medical prosthetic material to form an artificial trachea. The medical prosthetic material is composed of a woven fabric, a knitted fabric or a nonwoven fabric.

Figure 6:
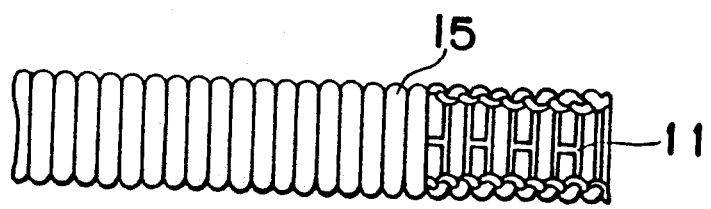
FIG. 6 is a partially cut-away view of an artificial blood vessel according to the present invention.

FIG. 6 shows an artificial blood vessel according to the present invention. This artificial blood vessel is composed of a tubular supporting frame 1 and a union cloth 15 spirally wound thereon to form a tubular wall of the artificial blood vessel. The union cloth 15 comprises absorbable macromolecular yarns and non-absorbable macromolecular yarns. The above union cloth may be replaced with a non-woven fabric.

The artificial blood vessel may be provided on its outer surface with a coating of a protein such as collagen or gelatin, and on its inner surface with a coating of an anti-thrombogenic material.

When such an artificial blood vessel is implanted in the body, one of the constituents of the tubular wall, i.e., absorbable macromolecular yarns are decomposed and absorbed in the body, thereby forming pores between non-absorbable macromolecular yarns. The granulation tissues enter into the pores so that the artificial blood vessel adheres to the surrounding tissues and is fixed thereto. Since the medical prosthetic material is composed of union fabric with a high density, the artificial blood vessel is airtight and watertight. Thus, the artificial blood vessel is initially stiffened, but it is softened gradually as the absorbable macromolecular yarns are dissolved and absorbed in the body. It is possible to minimize an obstacle due to implantation as well as to avoid occurrence of inflammation.

The construction of FIG. 1 may be applied to an artificial trachea, which comprises a tubular supporting frame as shown in FIG. 1, and a medical prosthetic material arranged on its inner and/or outer surfaces. In such a case, the supporting frame is generally formed with fluoroplastics so as to have an inner diameter of 20 to 30 mm, a length of 10 to 50 mm, and a thickness of 1 mm. The medical prosthetic material may be a woven fabric composed of absorbable macromolecular yarns and non-absorbable macromolecular yarns, as shown in FIG. 4. The outer surface of this artificial trachea may be coated with a protein such as collagen or gelatin.

Since the outer wall of such an artificial trachea is composed of a union fabric with a high density, it is kept airtight and water tight just after implantation of the artificial trachea so that the expired air and inspired air will not escape. Thus, the artificial trachea will fulfil the intended function effectively. Also, there is almost no occurrence of microbism as external bacteria are prevented from passing through the cloth. The absorbable macromolecular yarns constituting the union cloth is decomposed and absorbed in the body with the lapse of time to form openings in the tubular wall of the artificial trachea. For this reason, the granulation tissues enter into the openings formed between the remaining non-absorbable macromolecular yarns and encapsulate the artificial trachea to form a composite structure.

Figure 7:
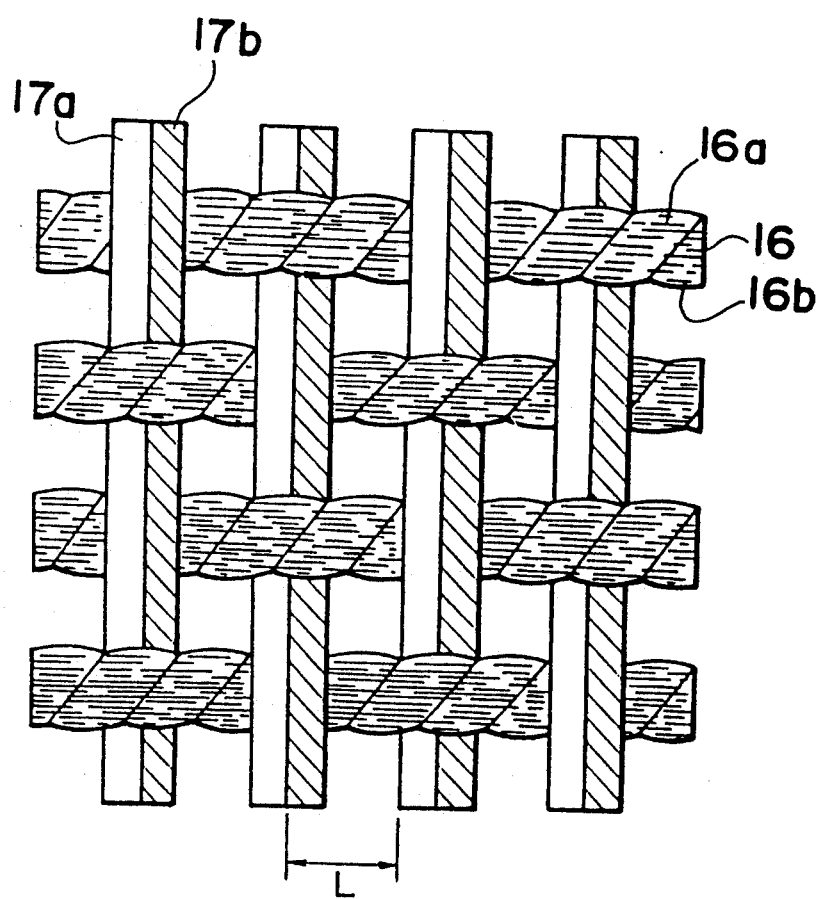
FIG. 7 is a fragmentary plan view of a medical prosthetic material composed of a woven fabric used in the artificial tubular organ according to the present invention.

FIG. 7 shows a weave pattern of a medical prosthetic material constructed by passing weft yarns 16 alternately under and over warp yarns 17 across the width of the fabric. The weft yarns 16 are twist yarns composed of a non-absorbable macromolecular yarn 16a and an absorbable macromolecular yarn 16b, while the warp yarns 17 are doubled yarns composed of a non-absorbable macromolecular yarn 17a and an absorbable macromolecular yarn 17b.

The above absorbable and non-absorbable macromolecular yarns may be monofilament yarns or multifilament yarns. It is however preferred to use false twist yarns to improve airtightness and flexibility of the cloth. Since the woven fabric is constructed by weaving two kinds of composite yarns, i.e., doubled yarns and twist yarns, the size of the openings to be formed in the plain weave fabric after implantation may be controlled by variation of fiber diameters of the absorbable and non-absorbable macromolecular yarns, by changing the distance between neighboring two warp yarns or weft yarns, or by changing the number of yarns constituting doubled yarns or twist yarns.

In the above embodiment, the medical prosthetic material is composed of a woven fabric including double yarns as the warp yarns, and twist yarns as the weft yarns, but it may be a woven fabric or a knitted fabric, of which both the warp yarns and weft yarns are composed of either double yarns or twist yarns. Also, it is possible to use, as the medical prosthetic material, woven fabrics or knitted fabrics in which either the warp yarns or weft yarns are composed of double yarns or twist yarns, while the other being composed of non-absorbable macromolecular yarns.

Figure 9:
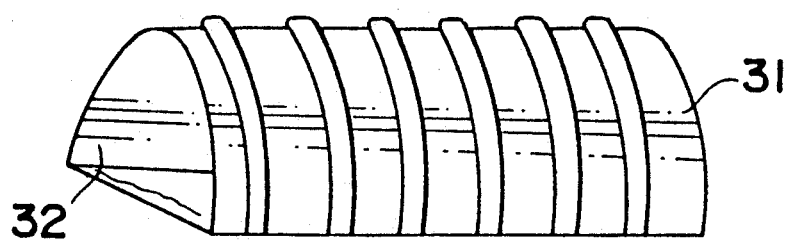
FIG. 9 is a diagrammatical perspective view of an artificial tubular organ of the prior art.

In the above case, it is preferred to use twist yarns which have a twist angle given by $\theta$ in FIG. 9, ranging from 45° to 88°, in particular, 65° to 85°.

It is preferred to use non-absorbable macromolecular yarns composed of single yarns having a diameter ranging from 0.1 to 100 $\mu$m, in particular, 1.0 to 40 $\mu$m. If the single yarns with a diameter exceeding 100 μm are employed, the woven fabric becomes rigid and causes inflammation after implantation of the artificial tubular organ. If the single yarns with a diameter of less than 0.1 μm are used, it is difficult to produce.

Figure 8:
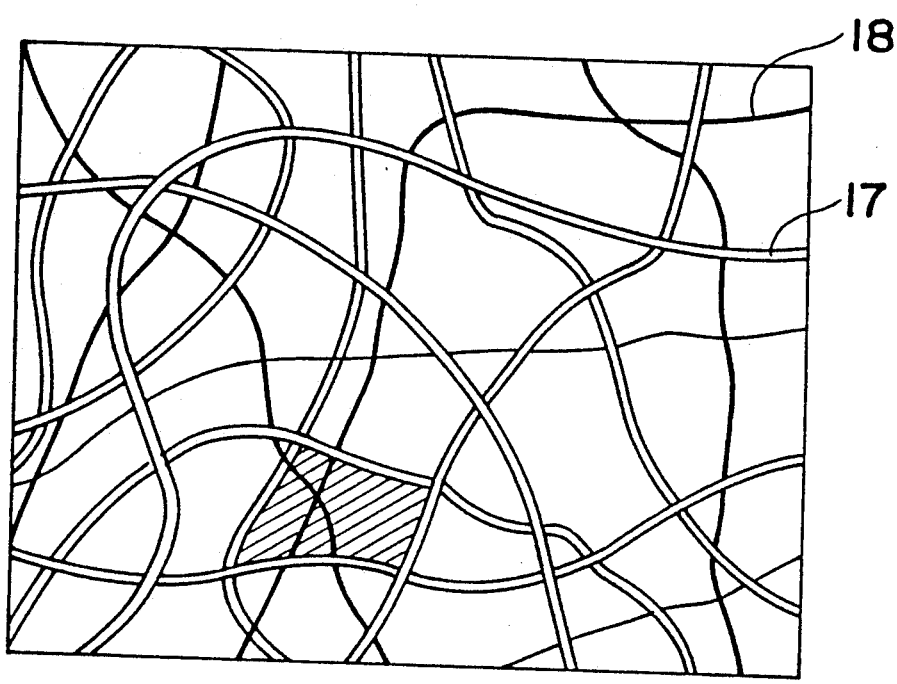
FIG. 8 is a fragmentary plan view of a medical prosthetic material composed of a nonwoven fabric used for an artificial tubular organ according to the present invention.

FIG. 8 is an enlarged fragmentary plan view of a nonwoven fabric used as a medical prosthetic material. This nonwoven fabric is composed of absorbable fibers 17 and non-absorbable fibers 18, which are intersected each other and interlocked at crossed points. The nonwoven fabric may be produced by a process comprising the steps of separately spinning an absorbable macromolecular material and an non-absorbable macromolecular material into filaments through nozzles, cutting the filaments into fibers, spraying the fibers onto a surface of a conveyer or a rotating surface of a columnar or cylindrical mandrel, and interlocking the resultant layered fibers at their crossed points by a physical process, for example, needling and water jet. The layered fibers may be interlocked at their crossed points by any other processes, for example, by heating, or by chemical treatment such as alkali treatment and solvent treatment. By spraying the fibers on the surface of the mandrel, it is possible to obtain a tubular nonwoven fabric by removing the mandrel from the product.

The fibers used for nonwoven fabric may be long fibers, or short fibers, or a combination of long fibers and short fibers. The nonwoven fabric is generally produced in the form of a flat or tubular shape.

It is preferred to use nonwoven fabrics with a bulk density of 0.005 to 0.60 g/cm$^3$ as a medical prosthetic material. If the bulk density of the nonwoven fabric exceeds 0.60 g/cm$^3$, the nonwoven fabric becomes rigid and causes inflammation resulting from implantation of the artificial tubular organ. If the bulk density is less than 0.005 g/cm$^3$ are used, the mechanical properties of the nonwoven fabric becomes lowered.

Also, it is preferred that the nonwoven fabric is at least 0.1 mm thick, in particular, 1 to 10 mm thick. If the thickness of the nonwoven fabric is less than 0.1 mm, durability becomes lowered.

It is preferred that the nonwoven fabric has an extension percentage of at least 5%, in particular, from 10 to 25%. The nonwoven fabric with such an extension percentage is particularly suitable for artificial tubular organs which is given the internal pressure, such as artificial blood vessels and artificial trachea.

EXPERIMENT 1

Figure 2:
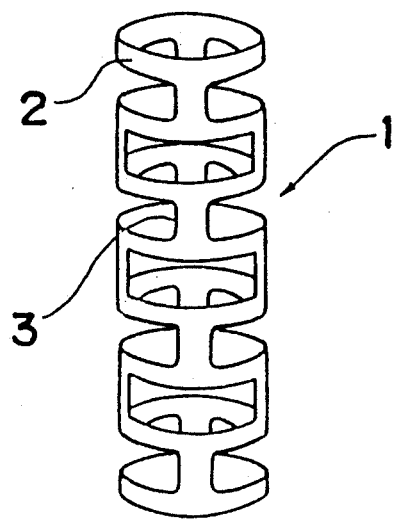
FIG. 2 is a perspective view of a supporting frame used in the artificial tubular organ of FIG. 1.

There were prepared artificial tracheae comprising a tubular supporting frame (23 mm outside diameter, 21 mm inside diameter, 60 mm length) of polytetrafluoroethylene having a structure as shown in FIG. 2, and a tubular mesh of polyester arranged in the lumen of the supporting frame and fixed thereto with stitches. The supporting frame is composed of ten ring portions and nine pairs of connecting portions (4 mm width by 4 mm length by 1 mm thick). The outermost ring portions are 4 mm in length, while other ring portions are 2 mm in length.

Using male dogs with the weight of 10 to 15 Kg, animal experiments were conducted by implanting each artificial trachea in the dog. Results are summarized in Table 1.

In the Table, early death means that the dog died within 4 weeks, while long-term survival means that the dog survived more than 4 weeks. The cause of death are classified into the following groups:

A: death caused by the supporting frame (e.g., deformation, migration);
B: death caused by the mesh (e.g., air leakage, supernumerary granulation);
C: death caused by surgical operation or trachea (e.g., stenosis or disherence at the anastomosed portion);
D: death caused by disease (e.g., obstruction of the airway caused by sputum);
E: death caused by inflammation; and
F: death caused by nacrosis.

COMPARATIVE EXPERIMENT 1

There were prepared artificial tracheae each comprising a supporting frame of polyethylene formed into a semi cylindrical form shown in FIG. 9 and covered with a mesh of polyester. Using male dogs with the weight of 10 to 14 Kg, animal experiments were conducted in the same manner as that in Experiment 1. Results are shown in Table 1.

COMPARATIVE EXPERIMENT 2

Figure 10:
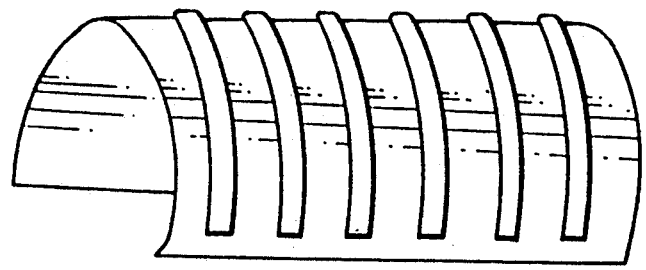
FIG. 10 is a diagrammatical perspective view of an another form of an artificial tubular organ of the prior art; and, FIG. 11 is a diagrammatical perspective view of a further form of an artificial tubular organ of the prior art.

There were prepared artificial tracheae each comprising a supporting frame of polyethylene formed into an arched shape shown in FIG. 10 and covered with a mesh of polyester. Using dogs with the weight of 7 to 13 Kg, animal experiments were conducted in the same manner as that in Experiment 1. Results are shown in Table 1.

COMPARATIVE EXPERIMENT 3

Figure 11:
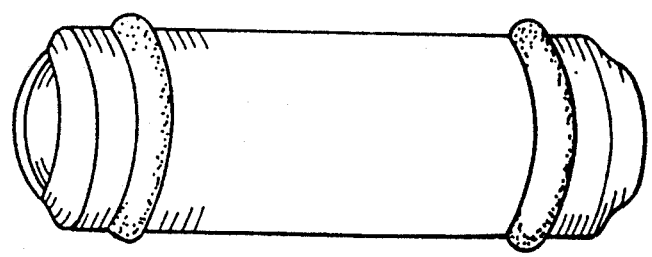

Using commercially available polyethylene tube (produced by Dow Chemicals) having a structure as shown in FIG. 11, animal experiments were conducted in the same manner as that in Experiment 1. The dogs used weighed of 9 to 13 Kg.

TABLE 1

| | Total Head | Early death | | long-time survival | | |
|---|---|---|---|---|---|---|
| | | Head | cause | Death | cause | survival |
| Ex. 1 | 28 | 13 | B: 10<br>C: 2<br>D: 1 | 4 | B: 1<br>C: 1<br>Victim: 1<br>Unknown: 1 | 11 |
| Comp. Ex. 1 | 20 | 8 | A: 1<br>B: 5<br>C: 2 | 12 | A: 4<br>B: 1<br>C: 6<br>Other: 1 | 0 |
| Comp. Ex. 2 | 5 | 0 | — | 5 | A: 5 | 0 |
| Comp. Ex. 3 | 10 | 2 | E: 1<br>F: 5 | 8 | A: 6<br>c: 2 | 0 |

From the results shown in Table 1, it is seen that there is no case in which death is caused by use of the supporting frame of the present invention. In contrast thereto, the artificial tracheae of comparative examples 1 and 2 cause death due to deformation of the supporting frame. On the other hand, the artificial tracheae of comparative Example 3 resulted in migration of the trachea. while the remaining head survived more than 4 weeks.

EXPERIMENTS 2-5

Using polyethylene terephthalate (herein after referred to as PET) yarns of 150 denier/30 filament and polyglycolic acid (herein after referred to as PGA) yarn of 120 denier/6 filament as weft yarns and warp yarns, there were prepared plain woven fabrics of 2/2 having a construction of FIG. 4. A distance (L) between neighboring PET yarns are varied as shown in Table 2. Each plain woven fabric was implanted in a subdorsal site of a dog, and the condition of implantation of the fabric was visually observed after 6 weeks have elapsed. Results are shown in Table 2.

In Table 2, "good" means that the fabric is fixed to the surrounding tissue by invasion of the granulation tissues into pores of the fabric, "better" means that the fabric is exfoliated from the surrounding tissue although the granulation tissues have invaded into pores of the fabric, and "bad" means that no invasion of granulation tissues into the pores of the fabric has been observed.

COMPARATIVE EXPERIMENTS 4-6

Using the same PET yarns as that of Experiments 2, there were prepared plain woven fabrics of 2/2 having a construction of FIG. 4, with a distance (L) between neighboring PET yarns being varied as shown in Table 2. Each plain woven fabric was implanted in a subdorsal site of a dog, and the condition of implantation of the fabric was visually observed after 6 weeks have elapsed. Results are shown in Table 2.

TABLE 2

|  | Distance (L) | Judgement |
|---|---|---|
| Ex. 2 | 307 μm | good |
| Ex. 3 | 241 μm | good |
| Ex. 4 | 153 μm | good |
| Ex. 5 | 126 μm | better |
| Comp. Ex. 4 | 101 μm | bad |
| Comp. Ex. 5 | 95 μm | bad |
| Comp. Ex. 6 | 74 μm | bad |

As will be understood from the results shown in Table 2, if the distance (L) between the neighboring PET yarns is less than 101 μm like as the fabrics of the comparative experiments, no invasion of the granulation tissues into the fabric occurs and the fabric is never fixed to the surrounding tissues.

EXPERIMENTS 6-9

Using a PET yarn of 70 denier/36 filament and a PGA yarn of 12 denier/6 filament or a PGA yarn of 6 denier/3 filament, there was prepared a doubled yarn to be used as a weft yarn for the plain woven fabric of FIG. 7 by yarn doubling. Also, there was prepared an S twist yarn to be used as a warp yarn for the plain woven fabric of FIG. 7 by twisting the above doubled yarn in the direction of S by 200 T/M. Using the resultant doubled yarn and S twist yarn, there were prepared plain woven fabrics of 1/1 having a construction of FIG. 7. A distance (L) between neighboring PET yarns are varied as shown in Table 3.

Each plain woven fabric was coated with a 10 wt % aqueous solution of collagen, dried and then implanted in a subdorsal site of a dog. After 6 weeks have elapsed, the condition of implantation of the fabric was visually observed. Results are shown in Table 3.

In Table 3, "good" means that the fabric is fixed to the surrounding tissue by invasion of the granulation tissues into pores of the fabric, "better" means that the fabric is exfoliated from the surrounding tissue although the granulation tissues have invaded into pores of the fabric, and "bad" means that no invasion of granulation tissues into the pores of the fabric has been observed.

COMPARATIVE EXPERIMENTS 7-8

Using PET yarns of 100 denier/36 filament, there were prepared plain woven fabrics of 1/1 having a construction of FIG. 7. A distance (L) between neighboring PET yarns was varied as shown in Table 3. Each plain woven fabric was implanted in a subdorsal site of a dog, and the condition of implantation of the fabric was visually observed after 6 weeks have elapsed. Results are also shown in Table 3.

TABLE 3

|  | PGA yarn | Distance (L) | Judgement |
|---|---|---|---|
| Ex. 6 | 12d/6f | 340 μm | good |
| Ex. 7 | 12d/6f | 281 μm | good |
| Ex. 8 | 12d/3f | 209 μm | good |
| Ex. 9 | 6d/3f | 147 μm | good |
| Comp. Ex. 7 | 6d/3f | 105 μm | bad |
| Comp. Ex. 8 | — | 95 μm | bad |

As will be understood from the results shown in Table 3, if the distance (L) between the neighboring PET yarns is less than 110 μm like as the fabrics of the comparative experiments, no invasion of the granulation tissues into the fabric occurs and the fabric is never fixed to the surrounding tissues.

EXPERIMENTS 10-13

Using PET and PGA as raw materials, there were prepared nonwoven fabrics by separately spinning PET and PGA with water jet into filaments through respective nozzles, and then cutting the filaments into fibers to form PET fibers with a diameter of 41.3 μm and PGA fibers with a diameter of 38.4 μm, spraying the resultant fibers onto a conveyer surface, and interlocking the resultant layered fibers at their crossed points by needling. The non-woven fabric has a thickness of 1.6 mm, and a bulk density of 0.12 g/cm$^3$. A mixing ratio of PET fibers to PGE fibers was determined such that the pores formed in the nonwoven fabric after decomposition of PAG fibers has an average diameter as shown in Table 4.

Each nonwoven fabric was coated with a 10 wt % aqueous solution of collagen, dried, and then implanted in a subdorsal site of a dog. After 6 weeks have elapsed, the condition of implantation of the fabric was visually observed. Results are shown in Table 4.

In table 4, "good" means that the fabric is fixed to the surrounding tissue by invasion of the granulation tissues into pores of the fabric, "better" means that the fabric is exfoliated from the surrounding tissue although the granulation tissues have invaded into pores of the fabric, and "bad" means that no invasion of granulation tissues into the pores of the fabric has been observed.

TABLE 4

|  | Amount of PGA fabric | Diameter of pores | Judgement |
|---|---|---|---|
| Ex. 10 | 74 | 310 μm | good |
| Ex. 11 | 59 | 225 μm | good |
| Ex. 12 | 43 | 162 μm | good |
| Ex. 13 | 32 | 134 μm | good |
| Comp. Ex. 9 | 15 | 108 μm | bad |

As will be understood from the results shown in Table 4, if the distance (L) between the neighboring PET yarns is less than 110 μm like as the fabrics of the comparative experiments, no invasion of the granulation tissues into the fabric occurs and the fabric is never fixed to the surrounding tissues.

EXPERIMENT 14

Using doubled yarns composed of a polypropylene (hereinafter referred to as PP) yarn of 75 denier/24 filament and a PGA yarn of 18 denier/6 filament as weft yarns and warp yarns, there were prepared tubular plain woven fabrics of 1/1 having a construction of FIG. 7 such that they have an inner diameter of 9 mm and a length of 6 cm. A distance (L) between neighboring PP yarns was 433 μm.

EXPERIMENT 15

Using doubled yarns composed of a high density polyethylene (density: 0.96 g/cm$^3$, hereinafter referred to as PE) yarn of 70 denier/12 filament and a PGA yarn of 18 denier/6 filament as weft yarns and warp yarns, tubular plain woven fabrics of FIG. 7 were prepared in the same manner as that in Experiment 14. The distance (L) between neighboring PE yarns was 513 μm.

EXPERIMENT 16

Using doubled yarns composed of a PET yarn of 75 denier/24 filament and a PGA yarn of 18 denier/6 filament as weft yarns and warp yarns, tubular plain woven fabrics of FIG. 7 were prepared in the same manner as that in Experiment 14. The distance (L) between neighboring PET yarns was 396 μm.

EXPERIMENT 17

Using doubled yarns composed of a 66-nylon (hereinafter referred to as NY) yarn of 70 denier/36 filament and a PGA yarn of 18 denier/6 filament as weft yarns and warp yarns, tubular plain woven fabrics of FIG. 7 were prepared in the same manner as that in Experiment 14. The distance (L) between neighboring NY yarns was 421 μm.

The plain woven fabrics prepared in Experiments 14–17 were coated with a 10 wt % aqueous solution of collagen and then dried to form a thin layer of collagen on the outer surface of the tubular fabrics. Each tubular woven fabric was implanted in a thoracotrophic aorta descendens of a dog. After 3 months have elapsed, the condition of implantation of the tubular fabric was visually observed. Results are shown in Table 5.

In Table 5, "good" means the fact that a neo-membrane was observed on the inner wall of the tubular fabric, but the granulation tissue was never observed in the lumen of the tubular fabric, "better" means that short granulation tissues were observed on the periphery of the inner wall of the tubular woven fabric, and "bad" means the fact that the granulation tissues grow across the lumen of the tubular woven fabric.

TABLE 5

|  | Material of non-absorbable yarn | Judgement |
|---|---|---|
| Ex. 14 | PP | good |
| Ex. 15 | PE | good |
| Ex. 16 | PET | better |
| Ex. 17 | NY | better |

As will be understood from the above results, by using the tubular woven fabric composed of absorbable yarns and nonabsorbable yarns as a medical prosthetic material, it is possible to permit the formation of neo-membrane on the inner wall of the tubular fabric without causing the growth of the granulation tissue in the lumen of the tubular fabric.

What is claimed is:

1. An artificial tubular organ comprising:
a tubular supporting frame made of a plastic material, and a biocompatible material layer having airtightness arranged on said supporting frame so as to cover at least a portion of a surface of said supporting frame, said supporting frame comprising a plurality of ring portions arranged on an axis, and a plurality of pairs of connecting portions extending between adjacent ring portions so as to connect said ring portions to each other, a first group of alternating pairs of said connecting portions being diametrically arranged on said ring portions, a second group of remaining alternating pairs of said connecting portions being arranged such that a plane containing center lines of a pair of said second group is perpendicular to a plane containing center lines of a pair of said first group of diametrically arranged connecting portions, said biocompatible material layer comprising at least one fabric selected from the group consisting of woven fabrics, nonwoven fabrics, and knitted fabrics, wherein said fabric is partially absorbable in an organism such that the organism forms pores in the fabric, said pores having an average diameter of 300 to 1500 μm and a surface area which occupies at least 20% of a surface area of said fabric.

2. An artificial tubular organ according to claim 1, wherein said biocompatible material comprises a woven fabric comprising absorbable macromolecular yarns and nonabsorbable macromolecular yarns.

3. An artificial tubular organ according to claim 2, wherein the woven fabric comprises double yarns or twist yarns comprising at least one absorbable macromolecular yarn and at least one nonabsorbable macromolecular yarn.

4. An artificial tubular organ according to claim 2, wherein said nonabsorbable macromolecular yarns comprise fibers made of a material selected from the group consisting of polyesters, polyolefins, polyamide resins, fluoroplastics, chlorine resins, polyurethane resins, cellulose derivatives, and natural fibers.

5. An artificial tubular organ according to claim 2, wherein said nonabsorbable macromolecular yarns comprise polyolefin fibers.

6. An artificial tubular organ according to claim 2, wherein said biocompatible material is coated with a protein.

7. An artificial tubular organ according to claim 6, wherein said protein is selected from the group consisting of collagen, gelatin, fibrinogen, globulin and fibronectin.

8. An artificial tubular organ according to claim 2, wherein said absorbable macromolecular yarns are formed from a material selected from the group consisting of polylactide, polyglycolic acid, polyvinyl alcohol, polyacryl amide, polyvinyl pyrolidone, poly-γ-methyl-glutamade, poly-caprolactone, polydioxanone, ethylene-carbo monoxide copolymers, cellulose derivatives, cellulose copolymers, and vinyl acetate-unsaturated carboxylic acid copolymers.

9. An artificial tubular organ according to claim 1, wherein the fabric is a nonwoven fabric comprising absorbable macromolecular fibers and nonabsorbable macromolecular fibers.

10. An artificial tubular organ according to claim 9, wherein said nonabsorbable macromolecular fibers comprise a material selected from the group consisting of polyesters, polyolefins, polyamide resins, fluoroplastics, chlorine resins, polyurethane resins, cellulose derivatives, and natural fibers.

11. An artificial tubular organ according to claim 10, wherein said nonabsorbable macromolecular fibers comprise polyolefin fibers.

12. An artificial tubular organ according to claim 9, wherein said absorbable macromolecular yarns are formed from a material selected from the group consisting of polylactide, polyglycolic acid, polyvinyl alcohol, polyacryl amide, polyvinyl pyrolidone, poly-γ-methylglutamade, poly-caprolactone, polydioxanone, ethylene-carbo monoxide copolymers, cellulose derivatives, cellulose copolymers, and vinyl acetate-unsaturated carboxylic acid copolymers.

13. An artificial tubular organ according to claim 1, wherein said biocompatible material is coated with a protein.

14. An artificial tubular organ according to claim 13, wherein said protein is selected from the group consisting of collagen, gelatin, fibrinogen, globulin and fibronectin.

15. An artificial tubular organ according to claim 1 wherein the surface area occupied by said openings or pores is 40 to 70% of the surface area of said fabric.

16. An artificial tubular organ according to claim 1, wherein the surface area occupied by said pores is 40 to 70% of the surface area of said fabric.

17. An artificial tubular organ according to claim 1, wherein said artificial tubular organ has a Y-shaped form comprising three interconnected tubular supporting frames.

18. An artificial tubular organ comprising:
a tubular supporting frame made of a plastic material, and a biocompatible material layer arranged on said supporting frame so as to cover at least one surface of said supporting frame, said supporting frame comprising a plurality of ring portions arranged on an axis, and a plurality of pairs of connecting portions extending between adjacent ring portions so as to connect said ring portions to each other, a first group of alternating pairs of said connecting portions being diametrically arranged on said ring portions, a second group of remaining alternating pairs of said connecting portions being arranged such that a plane containing center lines of a pair of said second group is perpendicular to a plane containing center lines of a pair of said first group of diametrically arranged connecting portions, said biocompatible material comprising at least one fabric selected from the group consisting of woven fabrics, nonwoven fabrics, and knitted fabrics, wherein said fabric is partially absorbable in the organism to form pores therein, said pores having an average diameter of at least 110 μm and a surface area which occupies at least 20% of the surface area of said fabric.

19. An artificial tubular organ according to claim 18, wherein said biocompatible material layer is coated with a protein that is selected from the group consisting of collagen, gelatin, fibrinogen, globulin and fibronectin.

20. An artificial tubular organ according to claim 18, wherein the surface area occupied by said pores is 40 to 70% of the surface area of said fabric.

21. An artificial tubular organ according to claim 18, wherein said artificial tubular organ has a Y-shaped form comprising three interconnected tubular supporting frames.

22. An artificial tubular organ according to claim 18, wherein said openings or pores have an average diameter of 300 to 1500 μm.

* * * * *